April 7, 1959 M. L. BROOKS Plant Pat. 1,825
ROSE PLANT
Filed July 30, 1958
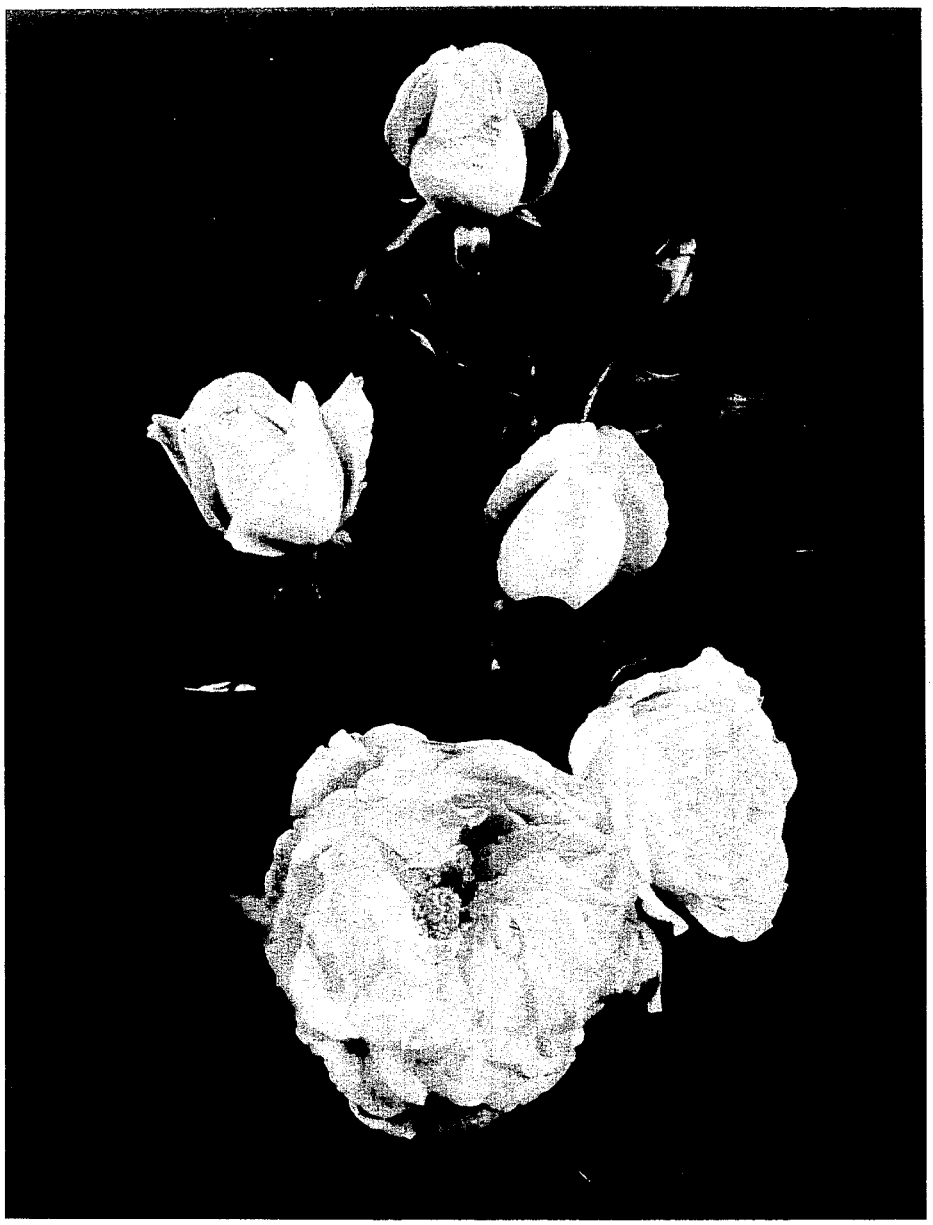
INVENTOR
M. L. Brooks
BY Robb & Robb
ATTORNEYS United States Patent Office Plant Pat. 1,825
Patented Apr. 7, 1959

1,825

ROSE PLANT

Munsey L. Brooks, Winona, Tex.

Application July 30, 1958, Serial No. 752,152

1 Claim. (Cl. 47—61)

The present invention relates to a new and distinct variety of rose plant of the hybrid tea class, which was discovered by me as a sport of the variety known as "The Doctor" (unpatented).

I discovered the new variety in one of my cultivated fields near Winona, Texas, when I was growing plants of the variety "The Doctor." While crossing the field, my attention was attracted to one plant on which there were white blooms, instead of the normal pink blooms customarily borne by the parent variety. Upon close examination of this plant, I found that one of the plants of the variety "The Doctor" had sported, and I thereupon took steps to carefully preserve the sport, keep it under observation, and to later asexually reproduce the same. These observations and asexual reproductions, as performed by me by budding in my fields near Winona, Texas, conclusively established that the white color of the blooms borne by the new sport was fixed and established, and capable of being transmitted through succeeding propagations.

In addition to the white blooms referred to in the foregoing, my new sport is characterized by the relatively large size and excellent and attractive form of the blooms. Otherwise, the new variety is generally similar to its parent, "The Doctor," but it is definitely distinguished therefrom, as well as from all other varieties of which I am aware.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Nickerson's Color Fan (American Horticultural Council), or Wanscher's Flower Color Chart, except where general color terms of ordinary dictionary significance are obvious:

Type: Hardy; bush; outdoor; sport; for garden decoration.
Class: Hybrid tea.
Parentage: Sport of "The Doctor."
Propagation: Holds its distinguishing characteristics through succeeding propagations by budding.

*Flower*

Locality where grown and observed: Near Winona, Texas.
Continuity: Continuous.
Fragrance: Strong. Nature—spicy.
Flowers borne: Singly; on strong stems of medium length.
Quantity of bloom: Free, outdoors.
Bud:
*Peduncle.*—Medium length; medium caliper; stiff; medium smoothness; with few yellow-brown prickles. Color—medium green.
*Before calyx breaks.*—Size—large. Form—pointed; with foliaceous appendages on the surface of the bud; with slender, bristle-like foliaceous parts extending beyond the tip of the bud equal to ½ or more of its length. Color—Moderate Yellow-Green, Plate 5GY5/6 (Nickerson).
*As calyx breaks.*—Color—Brilliant Greenish-Yellow, Plate 7.5Y9/8 (Nickerson).
*As first petal opens.*—Size—large. Form—long; ovoid. Color: outside—Very Pale Greenish Yellow (Wanscher); inside—Very Pale Orange Yellow (Wanscher).
*Opening.*—Opens up well; is retarded in opening by cold, hot, wet or dry weather.
Bloom:
*Size.*—Large; from 4½ inches to 5½ inches.
*Petalage.*—Double (more petals but the stamens not hidden); from 30 to 35 petals; arranged irregularly.
*Form.*—High-centered at first, but becoming cupped; petals at first being loosely cupped and rolled outward, but later becoming very loosely cupped and rolled outward at maturity.
Petals:
*Texture.*—Medium thickness; with both inside and outside satiny.
*Shape.*—Outside—obovate. Intermediate—obovate, with one slight point. Inside—obovate, with apex flat.

This description of a newly opened flower was made from a rose grown outdoors in the month of May near Winona, Texas:

*Color.*—Outer petal: outside surface—white; inside surface—white. Intermediate petal: outside surface—white; inside surface—white. Inner petal: outside surface—white; inside surface—white.

This description was made from a rose that was open for three days outdoors in the month of May near Winona, Texas:

*Color.*—Outer petal: outside surface—white; inside surface—white. Inner petal: outside surface—white; inside surface—white.
*General color effect.*—Newly opened flower—white. 3-days open—white.
*Behavior.*—Drop off cleanly.
*Flower longevity.*—On bush in garden—5 days in May and October. Cut flowers grown outdoors and kept at living-room temperatures—6 days in October.

*Reproductive organs*

Stamens: Many; arranged irregularly about pistils. Color—Pale Orange-Yellow, Plate 7.5YR9/4 (Nickerson).
Filaments: Medium length; with anthers. Color—yellow.
Anthers: Medium size; open at various times. Color—yellow.
Pollen: Moderate abundance. Color—gold.
Pistils: Many.
Styles: Uneven; medium length; medium caliper; bunched.
Stigma: Color—white.
Ovaries: All enclosed in calyx.
Hips: Short; globular; very smooth; walls thin. Color—green.
Sepals: Permanent; moderate length; straight. Color—gray.
Seeds: None observed.

*Plant*

Foliage:
*Leaves.*—Compound of 3 to 5 leaflets; abundant; medium size; heavy; semi-glossy.

*Leaflets.*—Shape—ovoid; with apex acute. Base—obtuse. Margin—simply serrate.

*Color.*—Mature: upper surface—normal green; under surface—gray-green. Young: upper surface—moderately red; under surface—normal bronze-red.

*Rachis (the supporting stem of the compound leaf).*—Medium caliper. Upper side—grooved; hairy. Under side—moderately prickly.

*Stipules.*—Moderately short; medium width; with short points turning out at an angle of more than 45°.

*Disease and insect resistance.*—Medium; similar to that of the parent variety "The Doctor," as determined by comparison with the latter and with other varieties grown under comparable cultural conditions near Winona, Texas.

Growth:

*Habit.*—Bushy; much-branched.

*Growth.*—Moderately vigorous.

*Canes.*—Heavy.

*Main stems.* — Color — green. Thorns — several; medium length; straight; with short, narrow base. Prickles—few; color—brown-red. Hairs—none.

*Branches.*—Color—green. Thorns—several; medium length; straight; with short, narrow base. Prickles—few; color—reddish brown. Hairs—none.

*New shoots.*—Color—bronze red. Thorns—several; medium length; straight; with short, narrow base. Prickles—several; color—reddish. Hairs—none.

I claim:

A new and distinct variety of rose plant of the hybrid tea class, substantially as herein shown and described, characterized particularly as to novelty by the unique combination of large size, excellent and attractive form and distinctive white color of the flowers.

No references cited.